(12) United States Patent
Van Acht et al.

(10) Patent No.: US 8,610,593 B2
(45) Date of Patent: Dec. 17, 2013

(54) USER FEEDBACK ENGINE

(75) Inventors: Victor Martinus Gerardus Van Acht, Eindhoven (NL); Nicolaas Lambert, Eindhoven (NL); Gerd Lanfermann, Aachen (DE); Kai Eck, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 413 days.

(21) Appl. No.: 13/125,642

(22) PCT Filed: Oct. 19, 2009

(86) PCT No.: PCT/IB2009/054586
§ 371 (c)(1),
(2), (4) Date: Apr. 22, 2011

(87) PCT Pub. No.: WO2010/049843
PCT Pub. Date: May 6, 2010

(65) Prior Publication Data
US 2011/0193699 A1    Aug. 11, 2011

(30) Foreign Application Priority Data

Oct. 27, 2008  (EP) ..................................... 08167585

(51) Int. Cl.
*G08B 25/08*    (2006.01)
(52) U.S. Cl.
USPC ............. 340/691.3; 340/692; 482/8; 600/595

(58) Field of Classification Search
USPC ......... 340/692, 691.3–691.6, 573.1; 600/300, 600/587, 595; 482/8, 9
See application file for complete search history.

(56) References Cited

U.S. PATENT DOCUMENTS

| 4,867,442 | A |   | 9/1989 | Matthews |
| 5,327,117 | A | * | 7/1994 | Kohsaka ..................... 340/691.6 |
| 5,532,680 | A | * | 7/1996 | Ousborne ..................... 340/692 |
| 5,976,083 | A |   | 11/1999 | Richardson et al. |
| 6,251,048 | B1 |   | 6/2001 | Kaufman |
| 7,602,301 | B1 | * | 10/2009 | Stirling et al. ............. 340/573.1 |
| 2002/0022551 | A1 |   | 2/2002 | Watterson et al. |
| 2003/0088196 | A1 | * | 5/2003 | Steve ........................... 600/587 |
| 2006/0029198 | A1 | * | 2/2006 | Dorneich et al. .......... 379/88.22 |
| 2007/0156031 | A1 | * | 7/2007 | Sullivan et al. ............ 340/573.1 |
| 2007/0210908 | A1 | * | 9/2007 | Putterman et al. ............ 340/506 |

FOREIGN PATENT DOCUMENTS

WO        03039368 A1    5/2003

* cited by examiner

*Primary Examiner* — Thomas Mullen

(57) ABSTRACT

There is therefore provided a user feedback engine, comprising a message generation module for generating messages for a user; a queue management module for managing a queue of the generated messages; wherein each message includes respective values for a plurality of parameters including a priority, a period of validity and a non-repeat time; and wherein the queue management module manages the messages in the queue in accordance with the respective values.

16 Claims, 3 Drawing Sheets

USER FEEDBACK ENGINE

FIELD OF THE INVENTION

The invention relates to a user feedback engine and a method of operating the same, and in particular to a user feedback engine that manages the order in which messages are presented to a user.

BACKGROUND OF THE INVENTION

Recently, there have been efforts to develop systems to help in the rehabilitation of people who have suffered an injury or disability, and in particular to provide systems that can instruct the user to perform particular exercises, and that can then provide useful feedback to the user on their movements, without requiring a physiotherapist or other professional to be present. Of course, these systems can also be used in the presence of a physiotherapist or other professional to help them provide effective therapy to the user.

These computer-aided rehabilitation systems often include motion sensors, such as video cameras and suchlike, for monitoring the movements of the user during exercises, and a user feedback engine for analyzing the movements and for providing feedback to the user on their movements. The feedback can relate to specific instructions for the movement that the user is performing, for example "keep your back straight", "keep your shoulders horizontal", "keep your pelvis horizontal", "stretch your arm", "stretch your left leg" and "move slowly". The feedback can also include other messages such as the number of repetitions of the exercise remaining and/or the remaining time (for a stretch, say).

The feedback will usually be audible messages, in the form of pre-recorded audio clips or generated by a speech synthesizer, since other forms of feedback, such as a display, are cumbersome to use during some exercises or for some body postures.

However, a problem with giving spoken feedback (whether in the form of audio clips or generated by a speech synthesizer) to the user is that only one sentence can be spoken at a time. Multiple messages can be generated at once, or within a short timescale, so there is a need to manage the order and presentation of the messages to the user. In addition, if a subsequent message is put into a queue while a first message is presented to the user, the subsequent message may lose its validity, and it may no longer be appropriate to present the subsequent message to the user. In addition, it can be very annoying for the user to be repeatedly (i.e. within a short timescale) presented with the same message.

Therefore, there is a need for a user feedback engine and a method of operating the same that manages a queue of messages for presentation to the user.

SUMMARY OF THE INVENTION

According to a first aspect of the invention, there is provided a user feedback engine, comprising a message generation module for generating messages for a user; a queue management module for managing a queue of the generated messages; wherein each message includes respective values for a plurality of parameters including a priority, a period of validity and a non-repeat time; and wherein the queue management module manages the messages in the queue in accordance with the respective values.

Preferably, the queue management module is adapted to arrange messages in the queue in an order determined by their respective values for the priority parameter.

Preferably, the queue management module is adapted to manage the queue such that any message that has been in the queue for a period longer than the respective value for the period of validity is removed from the queue.

Preferably, for each message, the queue management module is adapted to determine if the same message has been previously generated by the message generation module or presented to the user within a period defined by the non-repeat time, and, if so, to discard the message.

Alternatively, for each message, the queue management module is adapted to determine if the same message has been previously generated by the message generation module or presented to the user within a period defined by the non-repeat time, and, if so, to place the message at the back of the queue.

Preferably, each message includes a respective value for a message type, and wherein the queue management module is adapted to determine if a message having the same value for the message type has previously been generated by the message generation module or presented to the user within a period defined by the non-repeat time, and, if so, to place the message at the back of the queue.

In one embodiment, the user feedback engine is suitable for use in a system that comprises one or more sensors.

In this embodiment, the message generation module is preferably adapted to generate messages in response to signals received from one or more sensors.

In a preferred embodiment, the system is a rehabilitation or exercise system, and the message generation module is adapted to compare the signals received from the one or more sensors with predetermined templates or patterns for movement and/or posture of a user, and to generate messages in response to the comparison.

Preferably, the message generation module is adapted to determine the value of at least one of the plurality of parameters for each message in response to the comparison.

Preferably, the message generation module is adapted to determine the value of the priority parameter for each message in response to an amount of deviation of the signals from the one or more sensors with the predetermined templates or patterns.

In an alternative embodiment, the system is a navigation system, and the message generation module is adapted to compare the signals received from the one or more sensors with a predetermined route, and to generate messages in response to the comparison.

In a further alternative embodiment, the user feedback engine is suitable for use in a computer system, and wherein the messages generated by the message generation module are warning or error messages.

A second aspect of the invention provides a rehabilitation or exercise system comprising a user feedback engine as described above.

According to a third aspect of the invention, there is provided a method of operating a user feedback engine, comprising generating messages for a user, the messages having respective values for a plurality of parameters including a priority, a period of validity and a non-repeat time; and managing a queue of the generated messages in accordance with the respective values.

According to a fourth aspect of the invention, there is provided a computer program product comprising computer program code that, when executed on a computer or processor, is adapted to perform the method as described above.

BRIEF DESCRIPTION OF THE DRAWINGS

The invention will now be described, by way of example only, with reference to the following drawings, in which.

DETAILED DESCRIPTION OF THE EMBODIMENTS

Although the invention will now be described with reference to a computer-aided rehabilitation or exercise system, it will be appreciated that the user feedback engine can be applied to any type of system in which messages are generated and presented to a user. For example, the invention can be used in ordering messages generated by a navigation system for a vehicle, in ordering error or warning messages generated by a computer system, or in ordering warning messages in an aircraft cockpit. Furthermore, the invention can be applied to systems that provide messages or notifications other than audio messages, such as text-based messages, or messages that are given via one or more single or multi-color lights or LEDs.

Figure 1:
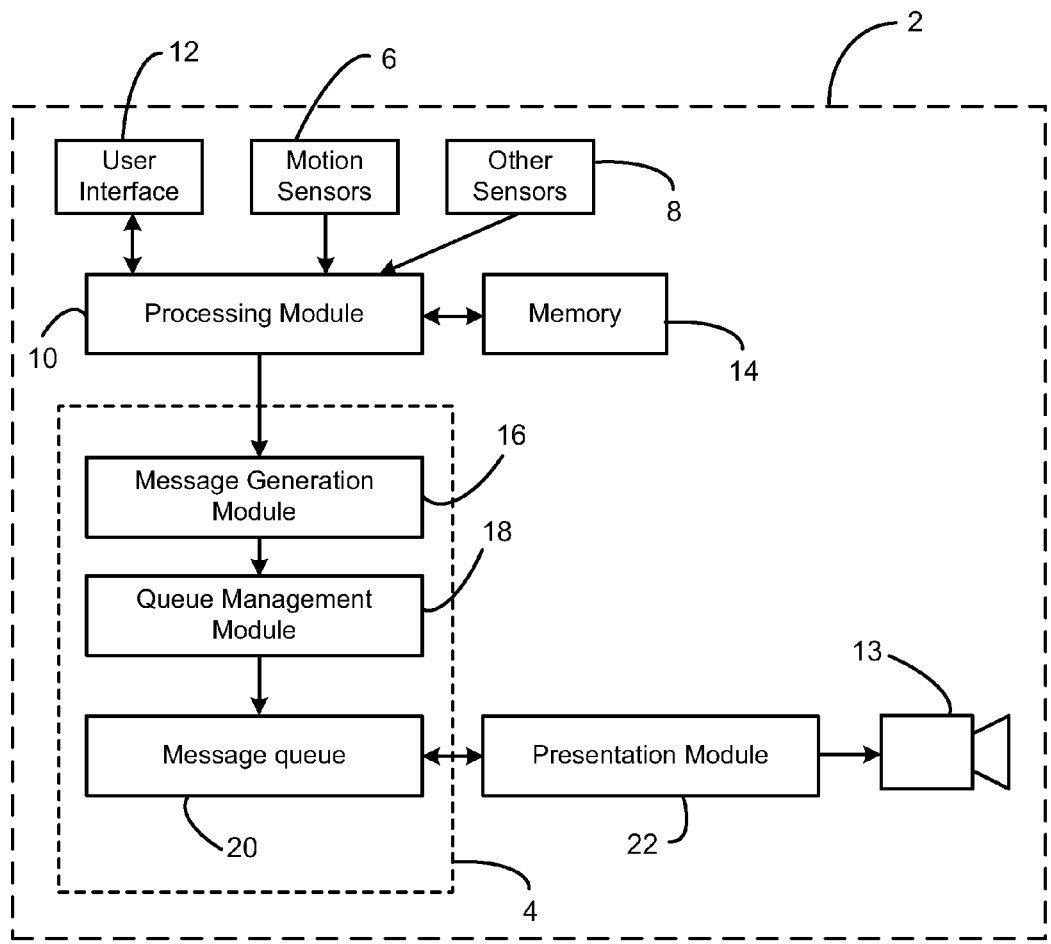
FIG. 1 is a block diagram of a computer-aided rehabilitation system including a user feedback engine in accordance with an embodiment of the invention.

A computer-aided rehabilitation system 2 comprising a user feedback engine 4 in accordance with an embodiment of the invention is shown in FIG. 1.

The system 2 also comprises motion sensor(s) 6 which monitor the motion of the user of the system 2. The motion sensor(s) 6 can comprise video cameras, inertial sensors that are to be attached to the user (such as accelerometers and gyroscopes), or any other suitable type of sensor. The system may also include other sensors 8 for monitoring physiological characteristics of the user, and these sensors 8 can include heartbeat sensors, blood pressure monitors, etc.

A processing module 10 receives the outputs of the motion sensor(s) 6 and other sensors 8.

A user interface 12 is provided to allow the input of various information into the system 2. For example, the interface 12 can be used to input personal characteristics of the user, such as familiarity of the user with the system 2, the physical condition of the user (for example the injury suffered, general health, etc.), the cognitive ability of the user, personal preferences for the user (such as an exercise program to be followed). The interface 12 can also be used to present instructions to the user via a display (for use prior to the start of the exercises), and/or can be used to present the audible feedback to the user. Alternatively, as shown in FIG. 1, a separate speaker 13 can be provided for presenting the audible feedback to the user.

A memory 14 is also provided that stores information required by the system 2 to operate. For example, the memory 14 can store information input by the user via the interface 12, different types of exercises and exercise programs, and detailed patterns and templates for the specific movements to be performed by the user. The format of this latter information depends on the type of motion sensor(s) 6 used in the system 2.

The processing module 10 uses the information stored in the memory 14 and the outputs from the motion sensor(s) 6 to determine the compliance of the user with an instruction to perform a specific movement or exercise. In particular, the processing module 10 can determine a deviation of various characteristics of the movement from a predetermined pattern or template for the movement (for example, a deviation of spinal curvature from that given in a template), and can determine the magnitude of this deviation.

Techniques for analyzing data from motion sensors such as cameras and inertial sensors to determine a deviation from template movements or patterns are well known in the art, and will not be described further herein.

The processing module 10 provides signals indicating the results of its analysis to the user feedback engine 4, and in particular to a message generation module 16.

The processing module 10 can also provide other signals to the user feedback engine 4, for example indicating the number of repetitions remaining for an exercise, and/or the time remaining for a stretch or exercise.

On receipt of the signals from the processing module 10, the message generation module 16 generates suitable messages for the user. The messages can relate to specific instructions for the movement that the user is performing, for example "keep your back straight", "keep your shoulders horizontal", "keep your pelvis horizontal", "stretch your arm", "stretch your left leg" and "move slowly". The feedback can also include other messages such as the number of repetitions of the exercise remaining and/or the remaining time (for a stretch, say).

As will be appreciated, the message generation module 16 generates messages based on the signals received from the processing module 10. For example, if the signals indicate that the user's spine is too curved, the message generation module 16 can generate a message indicating that the user should take corrective action, such as keeping their back straight.

As described above, the processing module 10 can determine the magnitude of the deviation of the movements of the user from a template or pattern for the exercise, and, in some embodiments, this deviation can be compared to a threshold by the message generation module 16 to determine if a message is to be generated.

Whenever a message is generated by the message generation module 16, it is passed to a queue management module 18 which places the message in a message queue 20. The operation of the queue management module 18 will be described further below with reference to FIGS. 3, 4 and 5.

If there is a message (or messages) in the message queue 20, a presentation module 22 retrieves the message at the front of the queue and presents the message to the user, via speaker 13.

The presentation module 22 can retrieve an audio clip from a memory (not shown) that corresponds to the message and play this to the user (or alternatively, the message can be generated by the message generation module 16 with the relevant audio clip included), or the presentation module 22 can include a speech synthesizer for synthesizing the audio message.

Figure 2:
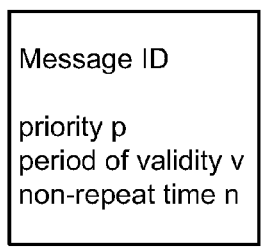
FIG. 2 illustrates a message structure in accordance with the invention.

FIG. 2 shows the structure of a message in accordance with the invention. The message comprises a Message ID, which identifies the particular message to be provided to the user, and values for a number of parameters.

In accordance with an aspect of the invention, at least three parameters are defined in each message, the parameters including a priority p, a period of validity v, and a non-repeat time n. The values of these parameters can be predefined for each specific message, or one or more of the values can be dynamically determined by the message generation module 16 in response to the signals from the processing module 10.

The priority p indicates how important the message is. The higher the priority, the more important it is for the message to be presented to the user.

The priority p of a particular message can be application dependent. There are, for example, movements that a user that has had a hip replacement should not do after their operation because this may damage the new hip joint (for example crossing their legs). Thus, messages that are related to those potentially damaging movements have a very high priority. Messages relating to improving the posture of the user during an exercise (for example "keep your back straight") are important, and have a high priority. Messages relating to, for example, the pace or tempo of the exercise, or the number of repetitions or time remaining have a much lower priority.

The value of the priority might also be influenced by how poorly the physiotherapy exercise is being executed by the user. As described above, the processing module 10 can determine the magnitude of the deviation of the movements of the user from a template or pattern for the exercise, and this deviation can be compared to a threshold by the message generation module 16 to determine if a message is to be generated. In addition or alternatively to comparing the magnitude of the deviation of the movements of the user from a template or pattern for the exercise to determine if a message is to be generated, the message generation module 16 can set the value of the message priority as a function of the magnitude of the deviation from the template or pattern. The larger the deviation, the higher the priority value should be set. Thus, the value of the priority can depend on the measurements from the motion sensors 6 and other sensors 8.

The period of validity, v, indicates how long the message is valid for, and thus how long the message can be present in the message queue 20. If a message has been present in the message queue 20 for a period longer than v (and therefore it has not be presented to the user), the message is no longer valid (i.e. the information conveyed by the message may no longer apply or be valid) and it should be removed from the message queue 20.

The validity of a message is dependent on the type or content of the message. For example, if a stream of messages are generated that represent a countdown of the remaining time (like "10", "8", "7", "6", "5", . . . ), the validity of each message will be one second. Another example relates to messages for correcting the movement of the user during an exercise—these messages should, at most, be valid until the end of that particular exercise.

The period of validity is often linked to the priority, with high priority messages having a longer period of validity.

The non-repeat time, n, represents a measure of how annoying it would be to the user for the message to be repeated, and indicates a period of time n in which the message should not be repeated. Thus, if a message has been generated with a non-repeat time n, and that same message was presented to the user n-m seconds ago (where $0<m\leq n$), the message should be discarded.

The annoyance caused by a message can depend on its content, tone and length. The non-repeat time can also depend on the importance of the message. For example, even if a message would otherwise be given a long non-repeat time (i.e. it is considered that repeating the message often would be annoying), if the message is particularly important, the non-repeat time may be reduced. Thus, in a way, the non-repeat time n can be linked to the priority p of the message.

Figure 3:
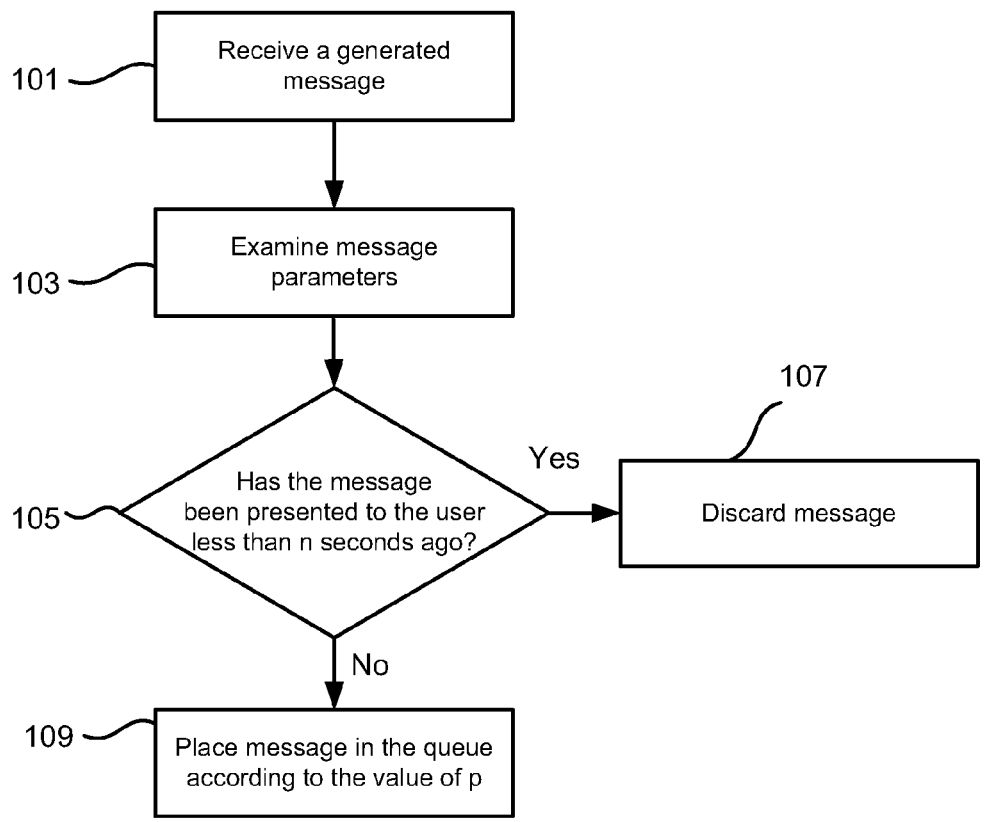
FIG. 3 is a flow chart illustrating a method of managing new messages in accordance with an embodiment of the invention.
Figure 4:
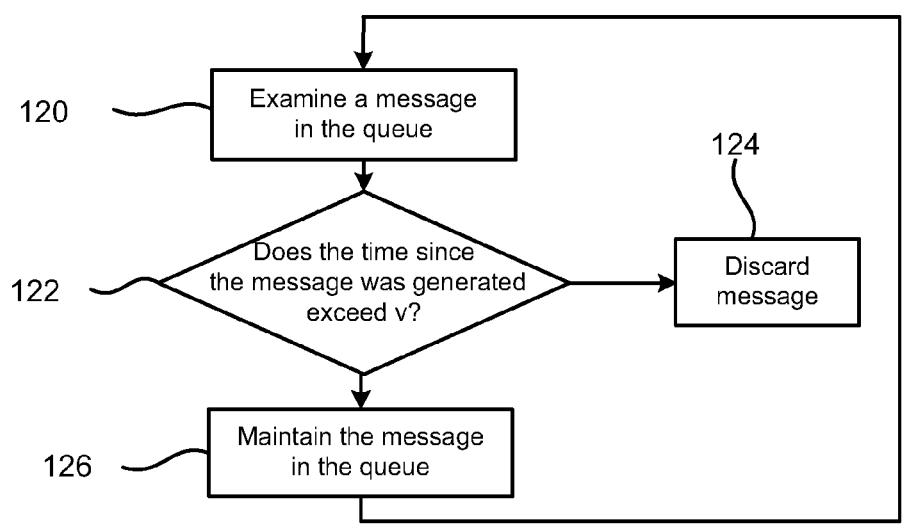
FIG. 4 is a flow chart illustrating a method of managing a queue of messages in accordance with an embodiment of the invention.

FIGS. 3 and 4 illustrate the operation of the queue management module 18 in accordance with an exemplary embodiment of the invention.

In step 101 of FIG. 3, the queue management module 18 receives a message that has been generated by the message generation module 16. In step 103, the queue management module 18 examines the values of the parameters of the message.

In particular, the queue management module 18 examines the value of the non-repeat time, n, and determines if that same message has been presented to the user less than n seconds ago (step 105). If the message has been presented less than n seconds ago, the message is discarded and does not form part of the message queue 20 (step 107). In an alternative embodiment, the queue management module 18 can determine if that same message has been generated less than n seconds ago, and, if so, the message can be discarded.

If the message has not been generated or presented less than n seconds ago, the queue management module 18 places the message in the queue in accordance with the value of the priority parameter, p (step 109).

Thus, the queue management module 18 examines the value of the priority parameter p of the other messages in the message queue 20, and places the new message at the appropriate position, so that messages with the highest priority are at the front of the queue 20.

In an alternative embodiment of the invention, instead of discarding the message in step 107, the queue management module 18 can place the new message at the end of the queue 20, to allow for the possibility that the non-repeat time parameter can be satisfied by presenting all of the other messages in the queue 20 to the user first.

The queue management module 18 continuously or periodically examines each of the messages in the queue 20 (step 120 of FIG. 4) to determine if they should remain in the queue 20. In particular, the queue management module 18 determines whether the time elapsed since a particular message was generated exceeds the value for the validity parameter, v (step 122). If the validity period has been exceeded, the message is discarded from the queue 20 (step 124).

If the validity period v has not been exceeded, the message is retained in its current position in the message queue 20 (step 126).

The method then returns to step 120 for the next message in the queue 20

It will be appreciated that the methods shown in FIGS. 3 and 4 are merely for illustration, and the queue management module 18 can check and utilize the values of the parameters of the messages in any desired order. For example, instead of considering the non-repeat time before the message is placed in the queue 20, the management module 18 can place the generated messages in the queue 20 in accordance with their priority value, and then consider the value of the non-repeat time parameter when the message reaches the front of the queue (i.e. when it is the next message to be presented to the user).

Figure 5:
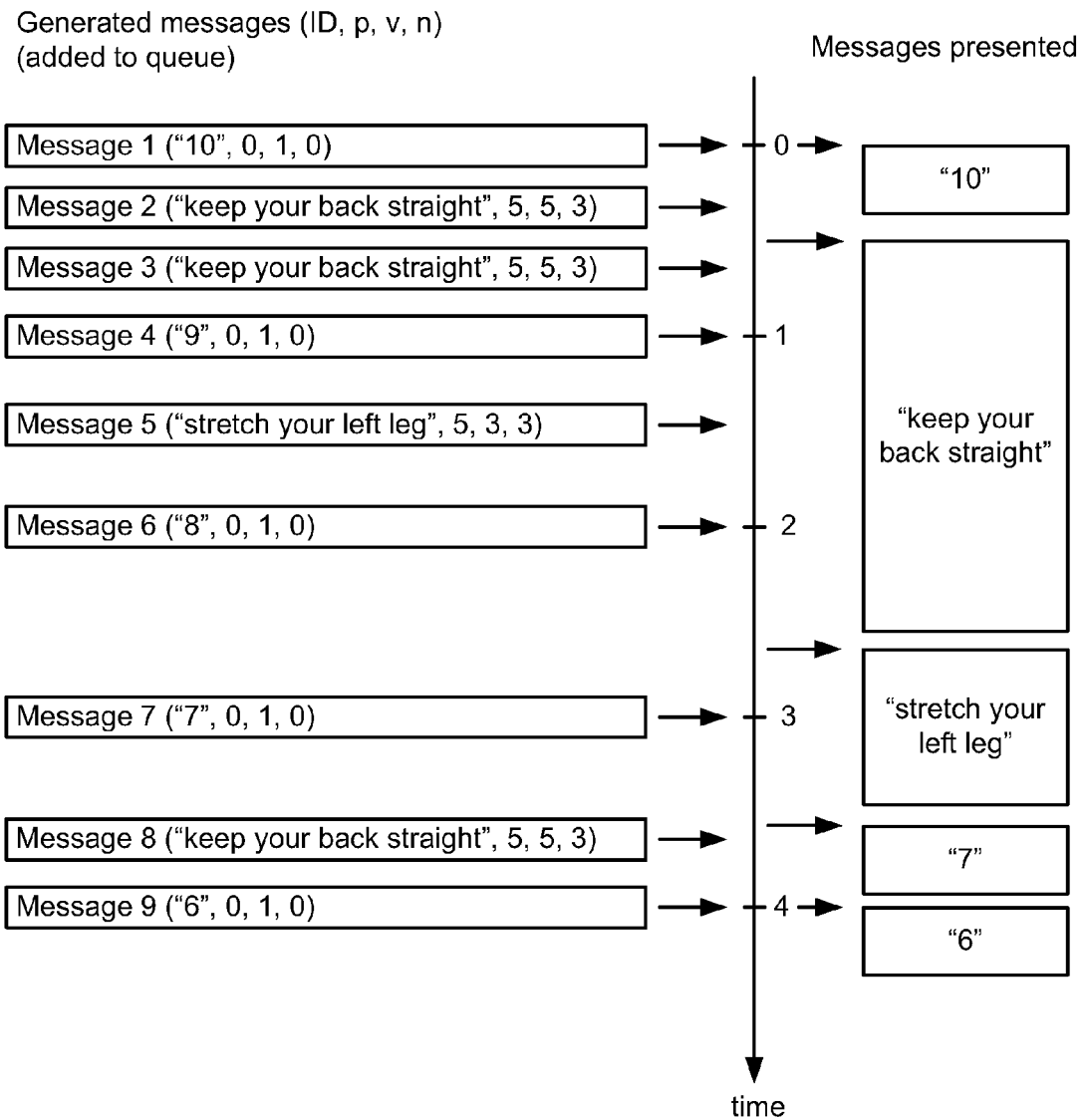
FIG. 5 is a timeline illustrating the generation and presentation of messages in accordance with an embodiment of the invention.

The operation of the invention will now be described with reference to FIG. 5. FIG. 5 is a timeline showing messages that could be generated by the rehabilitation system 2, including some exemplary parameter values, and the messages that actually get presented to the user. In this embodiment, a priority of 0 is considered to be a low priority, and a priority of 5 is considered to be a high priority.

At time t=0, a first message is generated, and this message is a timing indicator, indicating that 10 seconds are remaining in the exercise. This message has a validity of 1 second (v=1)

and a low priority (p=0). As this is the only message in the message queue 20, this message is presented to the user straight away.

As this message is being presented, a second message is generated (at time 0<t<1), instructing the user to keep their back straight. This message has a high priority (p=5), and relatively long non-repeat time (n=3) and a validity of 5 seconds (v=5). This message is placed at the front of the queue 20, since there are no other messages in the queue. Once the timing indicator "10" has been presented, the second message is presented to the user.

During this presentation, another "keep your back straight" message (message 3) is generated. However, as the non-repeat time (n=3) has been infringed (i.e. the first "keep your back straight" message is being presented to the user now), message 3 is discarded.

At time t=1, another timing indicator message is generated (indicating 9 seconds remaining). This message is placed into the queue 20 as message 2 is still being presented to the user.

Shortly after, a fifth message is generated, instructing the user to stretch their left leg. This instruction has a high priority (p=5), and so is placed into the queue 20 ahead of the timing indicator (message 4).

At time t=2, the queue management module 18 discards message 4 (the timing indicator for 9 seconds remaining) as its validity has been exceeded (v=1).

Also at time t=2, another timing indicator message is generated (message 6), indicating that there are 8 seconds remaining in the exercise. This message is placed into the queue after the "stretch your left leg" message (message 5), as the timing indicator has a lower priority.

At some time 2<t<3, the presentation of message 2 is completed, so the next message at the front of the queue is presented to the user. This message is the "stretch your left leg", as this message has a higher priority that message 6.

At time t=3, the queue management module 18 discards message 6 (the timing indicator for 8 seconds remaining) as its validity has been exceeded (v=1).

Also at time t=3, another timing indicator message is generated (message 7), indicating that there are 7 seconds remaining in the exercise. This message is placed into the queue 20 at the front (it is the only message in the queue 20 at this time).

At time 3<t<4, an eighth message is generated, indicating that the user should keep their back straight. However, as this message has previously been presented to the user within the non-repeat time (n=3), it is discarded by the queue management module 18.

Furthermore, at time 3<t<4, the presentation of the "stretch your left leg" message is completed, and the next message in the queue 20 can be presented. As the validity of message 7 (indicating 7 seconds remaining) has not been exceeded, this message is retrieved from the queue 20 and presented to the user.

At time t=4, the next timing indicator is generated (6 seconds remaining) and this is placed into the queue 20. As this is the only message in the queue, this message is then presented to the user on completion of the previous message.

In a further embodiment of the invention, instead of just applying the non-repeat time to a particular message (i.e. "keep your back straight"), the non-repeat time can be applied to any messages of the same type (i.e. posture instructions, movement instructions, number of remaining repetitions (in order to prevent the situation shown in FIG. 5 in which "7" is immediately followed by "6", etc.). In this embodiment, the message will be provided with another parameter, the message type, t, and the queue management module 18 will evaluate the non-repeat time for a particular message in view of other messages having the same value for the message type t.

There is therefore provided a user feedback engine and a method of operating the same that manages a queue of messages for presentation to the user While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality.

A single processor or other unit may fulfill the functions of several items recited in the claims. For example, some or all of the modules (processing module 10, message generation module 16, queue management module 18 and presentation module 22) can be implemented by a single processor or computer program.

The mere fact that certain measures are recited in mutually different dependent claims does not indicate that a combination of these measured cannot be used to advantage. Any reference signs in the claims should not be construed as limiting the scope. A computer program may be stored/distributed on a suitable medium, such as an optical storage medium or a solid-state medium supplied together with or as part of other hardware, but may also be distributed in other forms, such as via the Internet or other wired or wireless telecommunication systems.

The invention claimed is:

1. A user feedback engine, comprising:
   a message generation module for generating messages for a user;
   a queue management module for managing a queue of the generated messages;
   wherein each message includes respective values for a plurality of parameters including a priority, a period of validity and a non-repeat time; and wherein the queue management module manages the messages in the queue in accordance with the respective values.

2. A user feedback engine as claimed in claim 1, wherein the queue management module is adapted to arrange messages in the queue in an order determined by their respective values for the priority parameter.

3. A user feedback engine as claimed in claim 1, wherein the queue management module is adapted to manage the queue such that any message that has been in the queue for a period longer than the respective value for the period of validity is removed from the queue.

4. A user feedback engine as claimed in claim 1, wherein, for each message, the queue management module is adapted to determine if the same message has been previously generated by the message generation module or presented to the user within a period defined by the non-repeat time, and, if so, to discard the message.

5. A user feedback engine as claimed in claim 4, wherein each message includes a respective value for a message type, and wherein the queue management module is adapted to determine if a message having the same value for the message type has previously been generated by the message generation module or presented to the user within a period defined by the non-repeat time, and, if so, to place the message at the back of the queue.

6. A user feedback engine as claimed in claim 1, wherein, for each message, the queue management module is adapted to determine if the same message has been previously generated by the message generation module or presented to the user within a period defined by the non-repeat time, and, if so, to place the message at the back of the queue.

7. A user feedback engine as claimed in claim 1, that is suitable for use in a system that comprises one or more sensors.

8. A user feedback engine as claimed in claim 7, wherein the message generation module is adapted to generate messages in response to signals received from one or more sensors.

9. A user feedback engine as claimed in claim 8, wherein the system is a rehabilitation or exercise system, and the message generation module is adapted to compare the signals received from the one or more sensors with predetermined templates or patterns for movement and/or posture of a user, and to generate messages in response to the comparison.

10. A user feedback engine as claimed in claim 9, wherein the message generation module is adapted to determine the value of at least one of the plurality of parameters for each message in response to the comparison.

11. A user feedback engine as claimed in claim 10, wherein the message generation module is adapted to determine the value of the priority parameter for each message in response to an amount of deviation of the signals from the one or more sensors with the predetermined templates or patterns.

12. A user feedback engine as claimed in claim 7, wherein the system is a navigation system, and the message generation module is adapted to compare the signals received from the one or more sensors with a predetermined route, and to generate messages in response to the comparison.

13. A user feedback engine as claimed in claim 1 that is suitable for use in a computer system, and wherein the messages generated by the message generation module are warning or error messages.

14. A rehabilitation or exercise system comprising a user feedback engine as claimed in claim 1.

15. A method of operating a user feedback engine, comprising:
generating messages for a user, the messages having respective values for a plurality of parameters including a priority, a period of validity and a non-repeat time; and
managing a queue of the generated messages in accordance with the respective values.

16. A computer program product comprising computer program code that, when executed on a computer or processor, is adapted to perform the method as claimed in claim 15.

* * * * *